United States Patent
Redl et al.

(10) Patent No.: US 9,857,280 B2
(45) Date of Patent: Jan. 2, 2018

(54) METHOD FOR MEASURING COAGULATION OF BLOOD SAMPLES USING VISCOELASTIC TESTS (VET)

(71) Applicant: C A Casyso AG, Basel (CH)

(72) Inventors: Heinz Redl, Vienna (AT); Johannes Zipperle, Cambridge, MA (US); Wolfgang Holnthoner, Vienna (AT); Christoph Schlimp, Vienna (AT); Herbert Schochl, Vienna (AT)

(73) Assignee: C A Casyso AG, Basel (CH)

( * ) Notice: Subject to any disclaimer, the term of this patent is extended or adjusted under 35 U.S.C. 154(b) by 0 days.

(21) Appl. No.: 14/650,026

(22) PCT Filed: Dec. 6, 2013

(86) PCT No.: PCT/EP2013/075809
§ 371 (c)(1),
(2) Date: Jun. 5, 2015

(87) PCT Pub. No.: WO2014/086979
PCT Pub. Date: Jun. 12, 2014

(65) Prior Publication Data
US 2015/0316460 A1 Nov. 5, 2015

(30) Foreign Application Priority Data
Dec. 6, 2012 (EP) .................... 12195804

(51) Int. Cl.
*G01N 11/16* (2006.01)
*G01N 33/49* (2006.01)
*G01N 33/50* (2006.01)
*G01N 33/86* (2006.01)

(52) U.S. Cl.
CPC ............. *G01N 11/16* (2013.01); *G01N 33/49* (2013.01); *G01N 33/5064* (2013.01); *G01N 33/86* (2013.01)

(58) Field of Classification Search
CPC .... G01N 11/16; G01N 33/49; G01N 33/5094; G01N 33/86
See application file for complete search history.

(56) References Cited

PUBLICATIONS

Browder et al. "The Hemostatic System as a Regulator of Angiogenesis" 2000 Journal of Biological Chemistry, vol. 275, No. 3: 1521-1524.*

Amirkhosravi et al., "Determination of tumor cell procoagulant activity by Sonoclot analysis in whole blood," Thromb Res., 84(5):323-332, Dec. 1, 1996.
Fuchs et al., "Outgrowth endothelial cells isolated and expanded from human peripheral blood progenitor cells as a potential source of autologous cells for endothelialization of silk fibroin biomaterials," Biomaterials., 27(31):5399-5408, Epub Jul. 11, 2006.
Ganter et al., "Coagulation monitoring: current techniques and clinical use of viscoelastic point-of-care coagulation devices," Anesth Analg., 106(5):1366-1375, May 2008.
Gimbrone et al., "Human vascular endothelial cells in culture. Growth and DNA synthesis," J Cell Biol., 60(3):673-684, Mar. 1974.
Holcomb et al., "Admission rapid thrombelastography can replace conventional coagulation tests in the emergency department: experience with 1974 consecutive trauma patients," Ann Surg., 256(3):476-486, Sep. 2012.
Holnthoner et al. "Adipose-derived stem cells induce vascular tube formation of outgrowth endothelial cells in a fibrin matrix," J Tissue Eng Regen Med., Oct. 1, 2012.
Johansson et al., "Acute coagulopathy of trauma: balancing progressive catecholamine induced endothelial activation and damage by fluid phase anticoagulation," Med Hypotheses., 75(6):564-567, Epub Aug. 13, 2010.
Nielsen et al., "Qualitative thrombelastographic detection of tissue factor in human plasma," Anesth Analg., 104 (1):59-64, Jan. 2007.
Schöchl et al., "Goal-directed coagulation management of major trauma patients using thromboelastometry (ROTEM)-guided administration of fibrinogen concentrate and prothrombin complex concentrate," Crit Care., 14(2):R55, EpubApr. 7, 2010.
Shankarraman et al., "Standardized methods to quantify thrombogenicity of blood-contacting materials via thromboelastography," J Biomed Mater Res B Appl Biomater., 100(1):230-238, Epub Nov. 21, 2011.
Yu et al., "Carbohydrate structure dependent hemocompatibility of biomimetic functional polymer brushes on surfaces," Adv Healthc Mater., 1(2):199-213, Mar. 2012.
Zipperle et al., "A novel coagulation assay incorporating adherent endothelial cells in thromboelastometry," Thromb Haemost, 109(5):869-877, Epub Mar. 14, 2013.
International Search Report and Written Opinion for PCT/US2013/075809, dated Jan. 24, 2014, 10 pages.
International Preliminary Report on Patentability for PCT/US2013/075809, dated Nov. 13, 2014, 6 pages.
International Preliminary Report on Patentability for PCT/US2013/075809, dated Jan. 14, 2015, 6 pages.
European Search Report for Application No. 13799608.8 dated Jul. 14, 2015. 6 pages.
Extended European Search Report in European Application No. 17152097.6, dated Apr. 4, 2017, 5 pages.

* cited by examiner

*Primary Examiner* — Robert Yamasaki
*Assistant Examiner* — Teresa E Knight
(74) *Attorney, Agent, or Firm* — Fish & Richardson P.C.

(57) ABSTRACT

This disclosure provides a method for measuring coagulation of blood or plasma samples using viscoelastic tests (VET) wherein the measuring is performed in the presence of immobilized endothelial cells.

21 Claims, 5 Drawing Sheets

Figure 1:
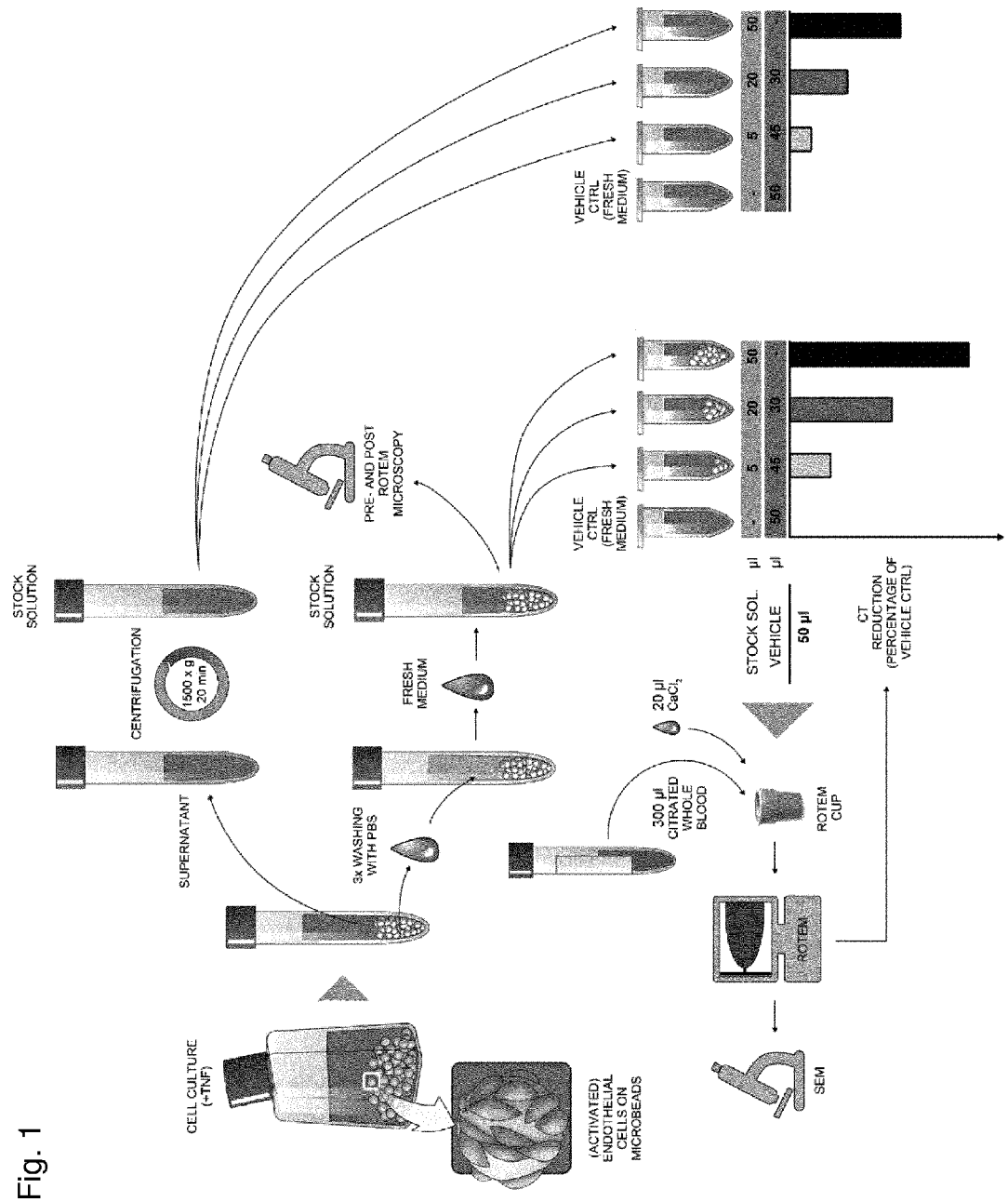

Fig. 3A
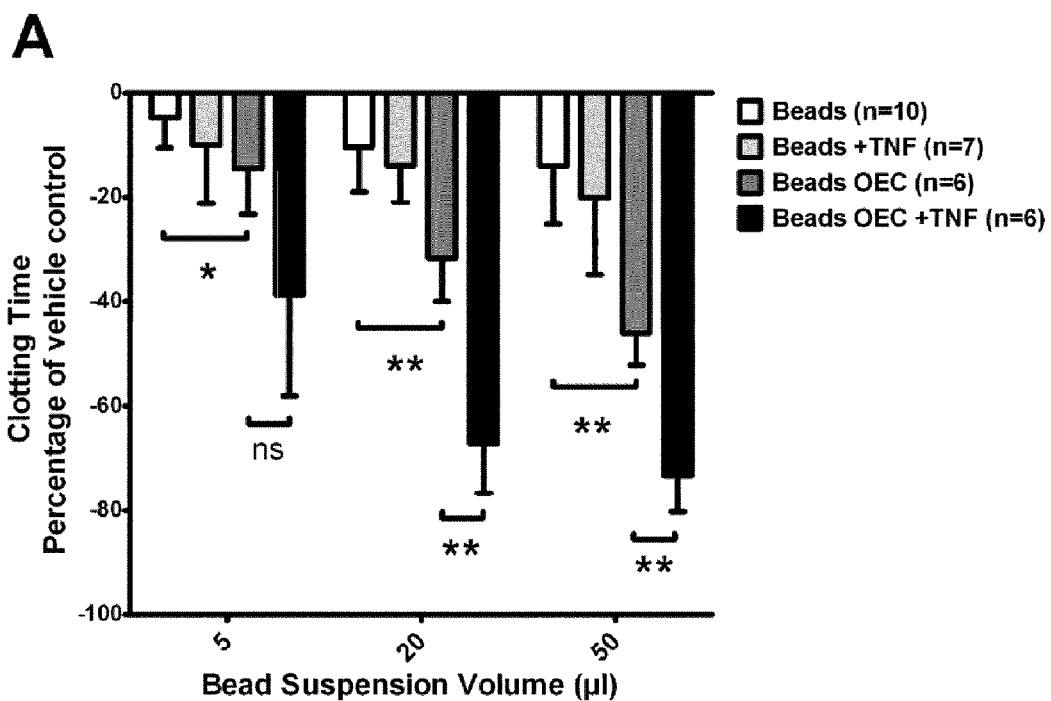
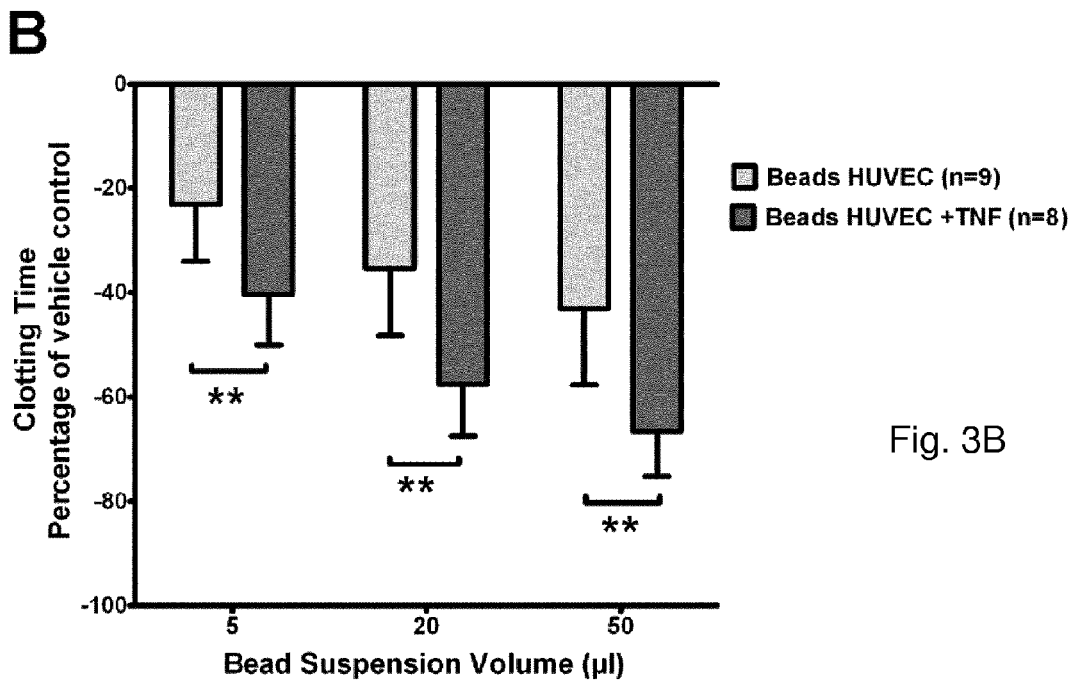
Fig. 3B

Fig. 5A
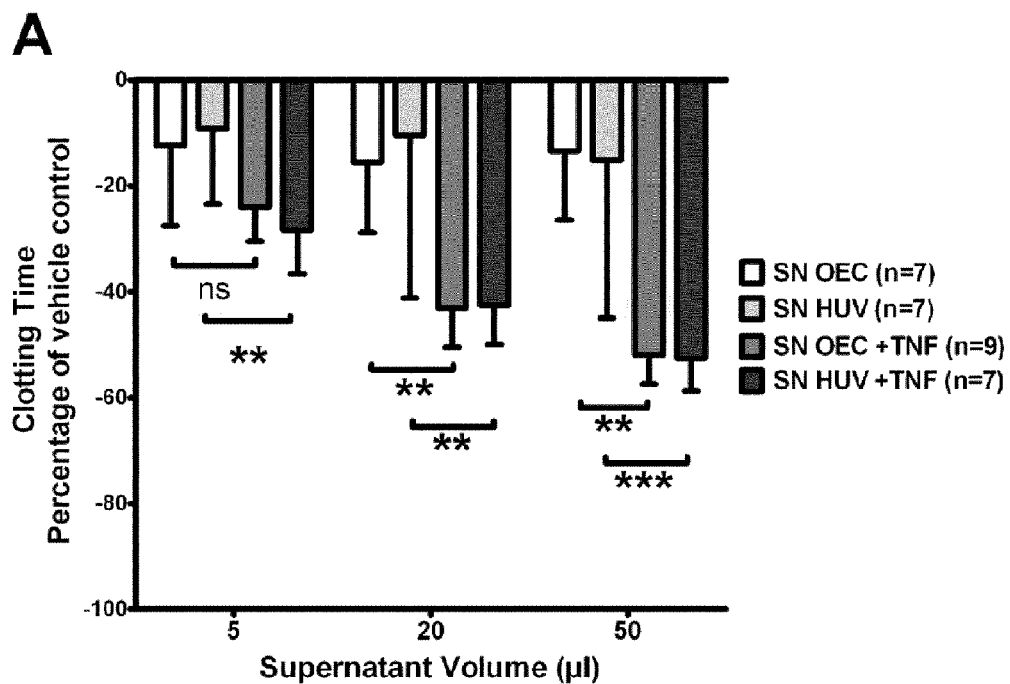
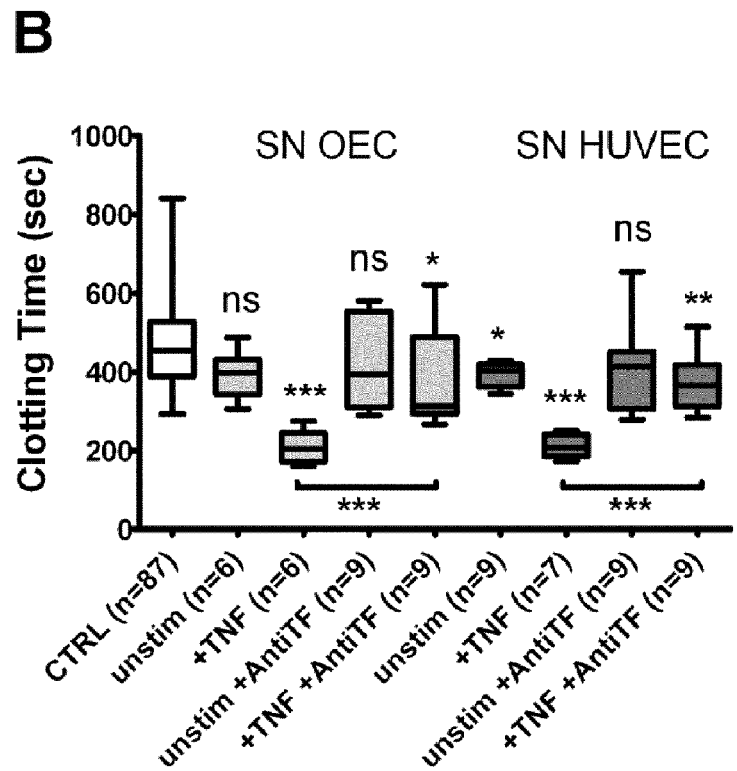
Fig. 5B

METHOD FOR MEASURING COAGULATION OF BLOOD SAMPLES USING VISCOELASTIC TESTS (VET)

CROSS REFERENCE TO RELATED APPLICATIONS

This application is a National Stage application under 35 U.S.C. §371 of International Application No. PCT/EP2013/075809, having an International Filing Date of Dec. 6, 2013, which claims the benefit of European Application No. 12195804.5 filed Dec. 6, 2012. This disclosure of the prior applications are considered part of (and are incorporated by reference in) the disclosure of this application.

The invention relates to methods involving viscoelastic tests (VET).

Hemostasis is a complex physiological process recruiting a wide range of plasmatic factors, blood cells and endothelium. The classical understanding of a large scale, cascade-like reaction driven by biochemical kinetics and dependent on isolated substrates has been replaced by a cell-based coagulation model. Following its initiation by TF-expressing cells like fibroblasts the coagulation process is amplified on the surface of activated platelets and leads to an accumulation of active proteases and cofactors that finally results in the burst formation of thrombin and the generation of fibrin. Clotting initiation, dynamics and breakdown depend on the availability of plasma coagulation factors but are also tightly regulated by cell-derived mediators. Recent studies claim for all components of haemostasis to be included in contemporary coagulation assays: plasma, blood and endothelial cells (Holcomb et al. Ann. Surg. 256 (2012): 476-486).

Routine laboratory tests analysing prothrombin time (PT) and activated partial thromboplastin time (aPTT) are performed using plasma in the absence of blood cells, which have been removed by centrifugation. Unlike routine laboratory tests, viscoelastic tests (VETs) such as rotation thromboelastometry (ROTEM) or thromboelastography (TEG) can be performed with whole blood, providing a more comprehensive overview of the coagulation process. VETs are widely used as a point-of-care monitoring tool to guide haemostatic therapies in the clinical setting (Ganter et al. Anesth. Analg. 106 (2008): 1366-1375).

TEG/ROTEM already deliver coagulation parameters that imply the impact of blood cells, but pro- and anticoagulant mediators derived from surrounding endothelium have yet not been included in VET. Activated endothelial cells are known to facilitate coagulation by expressing adhesion molecules, down regulating anti-thrombotic proteins, by expressing pro-coagulants and by releasing membrane vesicles.

However, besides the blood components present in such classical VETs (blood cells, platelets, plasma components, coagulation factors, coagulation modulators, etc.) also endothelial cells have a relevant influence on blood coagulation. There have been several demands by leading scientists in the present field to include the endothelial cell component into VETs (Holcomb et al. (2012); Johansson et al., Med. Hypoth. 75 (2010): 564-567), however, up to date, the direct influence of endothelial cells still cannot be investigated with the VETs currently available. An indirect influence of endothelial cells on VETs has been investigated by contacting blood with endothelial cells, removing the endothelial cells and measuring the blood coagulation afterwards by TEG (Shankarraman et al., J. Biomed. Mater. Res. (B) 100B (2012): 230-238); however, this test was intended to test the utility of using TEG to study the thrombogenicity of biomaterials. There is an ongoing need to provide such VETs observing the direct influence of endothelial cells on blood coagulation in the present field.

Amirkhosravi et al. (Throm. Res. 84 (1996): 323-332) discloses the determination of tumor cell procoagulant activity by SONOCLOT™ analysis in whole blood. Yu et al. (Adv. Healthc. Mat. 1 (2012): 199-213) report about carbohydrate structure dependent hemocompatibility of biomimetic functional polymer brushes on surface.

It is an object of the present invention to provide a method wherein also endothelial cells are incorporated into VETs.

Therefore, the present invention provides a method for measuring coagulation of blood or plasma samples using viscoelastic tests (VET) wherein the measuring is performed in the presence of immobilised endothelial cells.

With the present invention it is for the first time possible to analyse the direct influence of endothelial cells on blood coagulation in VETs. Accordingly, with the present invention, novel VETs are provided introducing endothelial cells carrying surfaces, especially microbeads, to measure the direct impact of endothelial cells on coagulation. When the method is performed with microbeads, the microbeads with the endothelial cells on their surface are suspended into the measurement cup of the viscoelastic test device and mixed with the blood or plasma sample. With the present method it is made possible that endothelial cells form part of the analysed, firming blood clot. The added endothelial cells are preferably adherent to a collagen surface, representing an adequate reproduction of the in vivo situation.

VETs are known for considerable time, including suitable VET devices for coagulation monitoring assessing the viscoelastic properties of blood. Established VETs include TEG and ROTEM with many variations available for these methods (see e.g. Gantner et al., 2008). VETs provide global information on the dynamics of clot development, stabilisation and dissolution that reflect in vivo haemostasis. VETs are frequently used as point-of-care tests to monitor patients in (complex major) surgery or trauma patients. Such monitoring has been shown to significantly reduce the use of blood component therapy and overall blood loss (see e.g. Schöchl et al., Crit. Care 14 (2010):R55).

Typical VETs are performed by adding whole blood to a heated cuvette at 37° C. Within the cup a pin is suspended connected to a detector system—this is a torsion wire in the case of TEG and an optical detector in the case of the ROTEM device. The cup and pin move relative to each other through an angle of 4° 45'. The movement is initiated from either the cup (TEG) or the pin (ROTEM). As the blood clots, fibrin strands form between the cup and pin and rotation of the cup is transmitted to the pin in the case of the TEG or impedes the rotation of the pin in the case of the ROTEM. The patterns of changes in strength and elasticity in the clotting blood provide information about how well the blood can perform hemostasis (the halting of blood flow), and how well or poorly different factors are contributing to clot formation.

Usually (at least) four values that represent clot formation are determined by this test: the R value (or reaction time), the K value, the angle and the MA (maximum amplitude). The R value represents the time until the first evidence of a clot is detected. The K value is the time from the end of R until the clot reaches 20 mm and this represents the speed of clot formation. The angle is the tangent of the curve made as the K is reached and offers similar information to K. The MA is a reflection of clot strength. A mathematical formula determined by the manufacturer can be used to determine a Coagulation Index (CI) (or overall assessment of coagulability) which takes into account the relative contribution of each of these 4 values into 1 equation. Although TEG originally involved fresh whole non-anticoagulated blood, both TEG and ROTEM commonly employ citrated whole blood that is re-calcified to initiate coagulation. It is also common to use an activator, such as tissue factor (TF), as this standardises the test and in addition speeds up the rate at which clotting takes place and hence the rate at which a result is generated TEG and ROTEM devices have a number of separate channels allowing a number of samples to be run simultaneously or sequentially.

Thromboelastometry (TEM) is also an established viscoelastic method for haemostasis testing in whole blood. TEM investigates the interaction of coagulation factors, their inhibitors, anticoagulant drugs, blood cells, specifically platelets, during clotting and subsequent fibrinolysis. The rheological conditions mimic the sluggish flow of blood in veins. While traditional TEG is a global assay for blood clotting disorders and drug effects, TEM is primarily used in combination with appropriate differential assays. They allow testing in the presence of therapeutic heparin concentrations and provide differential diagnostic information to support decisions in therapy. TEM detects both hypo- and hyperfunctional stages of the clotting process and is probably the only reliable rapid test for the diagnosis of hyperfibrinolysis. In contrast to standard clotting tests, the fibrin stabilizing effect of factor XIII contributes to the result. The rapid availability of results helps to discriminate surgical bleeding from a true haemostasis disorder and improves the therapy with blood products, factor concentrates, anticoagulants and protamine, hemostyptic and antifibrinolytic drugs. In a typical TEM, blood (300 µl, anticoagulated with citrate) is placed into the disposable cuvette using an electronic pipette. A disposable pin is attached to a shaft which is connected with a thin spring (the equivalent to Hartert's torsion wire in TEG) and slowly oscillates back and forth. The signal of the pin suspended in the blood sample is transmitted via an optical detector system. The test is started by adding appropriate reagents. The instrument measures and graphically displays the changes in elasticity at all stages of the developing and resolving clot. The typical test temperature is also here 37° C., but different temperatures can be selected, e.g. for patients with hypothermia. In contrast to TEG with its pendulum-like principle, the design of the TEM viscoelastic detection system makes it quite robust and insensitive against mechanical shocks or vibrations.

Commercially available VETs, especially various forms of TEG and ROTEM are disclosed e.g. in Ganter et al., 2008: Typically, blood samples are activated extrinsically (tissue factor) and/or intrinsically (contact activator). Furthermore, to determine fibrinogen levels, tests in the presence of a platelet inhibitor (e.g., cytochalasin D in fib-TEM) should be performed. This modified maximum amplitude/maximum clot firmness (MA/MCF) then represents the fibrin clot that developed without the contribution of platelets, i.e., the functional fibrinogen. It has been shown that the MA/MCF of these modified tests correlates well with the fibrinogen assessed by the Clauss method (r=0.85; TEG 5000 User Manual and r=0.7511). The traditional Clauss method, however, determines fibrinogen levels indirectly: Excess thrombin is added to diluted plasma, the time is measured until a clot develops and fibrinogen is calculated with the help of a calibration curve. Although the Clauss method is considered a standard assay, it has been shown that hemodilution with colloids may interfere with these assays, reporting falsely high levels of fibrinogen.

Preferred VETs are TEG, ROTEM, ReoRox™ and SONOCLOT™, especially TEG and ROTEM. Preferred TEGs are RapidTEG, TEG-Kaolin (with Kaolin as activator; for overall coagulation assessment and platelet function), TEG-Heparinase (using Kaolin and Heparinase for specific detection of heparin (i.e. a modified Kaolin test adding heparinase to inactivate present heparin), TEG-Platelet Mapping (ADP and arachidonic acid for platelet function, monitoring antiplatelet therapy (aspirin, ADP-, GPIIb/IIIa inhibitors), and TEG-Native (no activators/inhibitors added for a nonactivated assay; also used to run custom hemostasis tests). Preferred ROTEMs are ex-TEM (with TF for testing the extrinsic pathway; fast assessment of clot formation and fibrinolysis), in-TEM (with a contact activator for testing the intrinsic pathway; assessment of clot formation and fibrin polymerization), fib-TEM (with TF and a platelet antagonist for the qualitative assessment of fibrinogen levels), ap-TEM (with TF and aprotinin for assessing the fibrinolytic pathway; fast detection of fibrinolysis when used together with ex-TEM), Hep-TEM (with a contact activator and heparinase for specific detection of heparin (modified in-TEM test adding heparinase to inactivate present heparin), eca-TEM (with ecarin for the management of direct thrombin inhibitors (e.g., hirudin, argatroban)), tif-TEM (with 1:1000 TF for extrinsic pathway; monitoring recombinant activated factor VIIa), na-TEM (no activators/inhibitors added; nonactivated assay; also used to run custom hemostasis tests). Preferred Sonoclot assays are SonACT (with Celite for large-dose heparin management without aprotinin), kACT (with kaolin for large-dose heparin management with/without aprotinin), aiACT (with Celite and clay for large-dose heparin management with aprotinin (aprotinin-insensitive ACT)), gbACT(with glass beads for overall coagulation and platelet function assessment), H-gbACT (with glass beads and heparinase for overall coagulation and platelet function assessment in presence of heparin; detection of heparin), microPT* (with 1:1000 TF for assessment of the extrinsic pathway; monitoring recombinant activated factor VIIa), Native (no activators/inhibitors added; nonactivated assay; also used to run custom hemostasis tests).

As already disclosed above, the present invention for the first time enables the analysis of the direct influence of endothelial cells on blood coagulation in VETs. In Amirkhosravi et al., 1996, endothelial cells in suspension were added to whole blood in a VET. However in this set-up, these endothelial cells were used as controls for procoagulant tumor cells and not—as in the present invention—as a setup to simulate all three components of the blood circulation—blood plasma, blood cells and the by nature surrounding contact—adherent immobilized endothelial cells. With the present invention, for the first time a complete VET system was created to simulate these three elements of blood circulation. The breakthrough nature of the present invention is also reflected in the fact that the post-published corresponding article to the present application was published in a top journal of haematology in the scientific literature (Zipperle et al., Thromb. Haemost. 109 (2013): 869-877).

In contrast to the immobilized endothelial cells of the present invention the endothelial cells added in Amirkhosravi et al., 1996, (HUVECs) had (and were not intended to have) no effect on coagulation. This stands in sharp contrast to the teachings obtained with the present invention with immobilized endothelial cells. This surprising difference obtained between Amirkhosravi et al., 1996, and the present invention could be due to the fact that endothelial cells in their physiological environment form the innermost (confluent) layer of a blood vessel and are therefore naturally adherent cells (Gimbrone et al., J. Cell. Biol. 60 (1974): 673-684). To mimick this confluency the method according to the present invention was developed with immobilized cells adherent to surfaces, especially microbeads. The surfaces, especially the microbeads, enable a physiological coating and allow to study endothelial cells in a much more appropriate and practically relevant manner, because blood coagulation is much more closely mimicked. In addition to the fact that for studying adherent cells these cells have to be kept in an adherent manner, only the method according to the present invention has proven to allow technically reproducible results, because the immobilized cells can be used immediately and over a longer time period in contrast a free cell suspension (as applied by Amirkhosravi et al., 1996), which has to be specially prepared for each measurement by treating cells with enzymes (trypsin), subsequent washing, counting, and resuspension. This is not only laborious, but also not a stable system, since the adherent cells in the system of Amirkhosravi et al., 1996, will adhere to plastic surfaces within a few hours and no steady cell number can be achieved. This is in contrast to the present invention wherein endothelial cells are immobilised on surfaces (e.g. beads), which can be kept for several days/weeks with relatively stable cell numbers and immediate possibility of usage. The drawbacks of using endothelial cells in VETs were thereby elegantly circumvented by the method according to the present invention. Moreover, the use of these cells to more closely mimick in vivo blood coagulation has never been contemplated in the prior art, and of course not in Amirkhosravi et al., 1996 (in fact, this paper had a completely different objective).

In any way, it is essential that the endothelial cells are already provided in immobilised form for the VET according to the present invention; it is therefore clear that the use non-cell covered or substance coated microbeads (as examples for non-cell-coated surfaces) is not suitable for the method according to the present invention (uncoated microbeads have minor effects in the system according to the present invention and are only used as blank controls).

Preferably, the endothelial cells are immobilised on microbeads, preferably on dextran microbeads.

There are several types of cell microcarriers available, mostly for bioreactor applications. The spherical geometry provides a favourable surface to volume ratio and enables pipetting as well as a better dispersion of the carriers within moving cell culture containers. Core materials for microcarrier manufacturing include glass, polystyrene, polypropylene, acrylamide, porcine gelatine, dextrane etc. Biopolymeres like dextrane are capable of being chemically cross-linked to other large organic molecules like collagen and are therefore advantageous for simulating cell adherence on a basal lamina. In this concern, collagen-coated biomaterials have been shown to possess a relatively low thrombogenecity when exposed to blood (Shankarraman et al., J. Biomed. Mater. Res. (B) 100B (2012): 230-238). Microbeads are uniform polymer particles with 0.1 to 1000, preferably 0.5 to 500 micrometers in diameter. Endothelial cells can be seeded onto their surface, and used according to the present invention. In one embodiment, the disclosed microbeads may be irregularly shaped microbeads or regularly shaped microbeads. The microbeads may also have a shape selected from the group consisting of microspheres, microcapsules, microrods, microcubes and microtubes.

Most preferably, said microbeads are microspheres. If a large surface area is desired, the microbeads may also be porous. Preferably, the microbeads are made of more than one material, for example mixtures of two, three or more different materials, especially of the materials mentioned above. Even more preferred are microbeads which are coated, for example dextran or cross-linked dextrans which are coated with fibronectin, albumin, polylysine or natural polymers, such as collagen, fibrin, alginate, chitosan, gelatine etc. Binding of the endothelial cells to the microbeads is performed according to methods known in the art for binding cells to solid surfaces, especially microbeads. Preferably, the surface is "attractive" for endothelial cells so that the endothelial cells adhere to this surface, e.g. by integrin binding.

Although all types of endothelial cells can in principle be used in the method according to the present invention (more specifically: microvascular or macrovascular endotheial cells), preferrred endothelial cells used in the present method are outgrowth endothelial cells (OECs), human umbilical vein endothelial cells (HUVECs), human dermal microvascular endothelial cells (HDMECs; as a model for microvascular endothelial cells) or human saphenous vein endothelial cells (HUVECs; as a model for macrovascular endothelial cells).

Preferably, the method according to the present invention is performed with blood and cells obtained from the same donor (autologous setting). However this is not mandatory as pooled HUVECs and OECs had the same effect on viscoelastic parameters. This shows that several endothelial cell types can be seeded onto microbeads to include the endothelial portion of hemostasis in VETs. When provided under conditions that enable the transport of live cells (i.e. quick-frozen), the endothelium-coated beads can conveniently be provided as a test kit.

The present invention is focused on the direct impact of endothelial cells in VETs. With the present invention a novel method to include adherent ECs in VETs, especially thromboelastometry tests, to assess its impact on coagulation parameters is introduced and validated.

According to another aspect, the present invention relates to a kit comprising a device for performing viscoelastic tests (VETs) and immobilised endothelial cells, especially for performing the method according to the present invention. Accordingly, the kit according to the present invention comprises at least two distinct elements, the device for performing VETs and the immobilised endothelial cells. It is also not possible to immobilise endothelial cells e.g. in the measurements cups of ROTEM or TEG, because the measurement principle is the formation of fibrin fibres between two rough surfaces and immobilization of endothelial cells on the cup wall would prevent this contact, such no signal could be measured. This kit for the first time enables a diligently working mimick for in vivo blood coagulation processes.

The device for performing viscoelastic tests (VETs) may be any device used for known VETs; virtually all VET devices (especially the preferred ones described above) can be used with the immobilised endothelial cells according to the present invention.

The invention is further disclosed in the following examples and the figures, yet without being restricted thereto.

FIG. 1 shows the schematic work flow chart of the bead preparation and measurement procedure.

Figure 2:
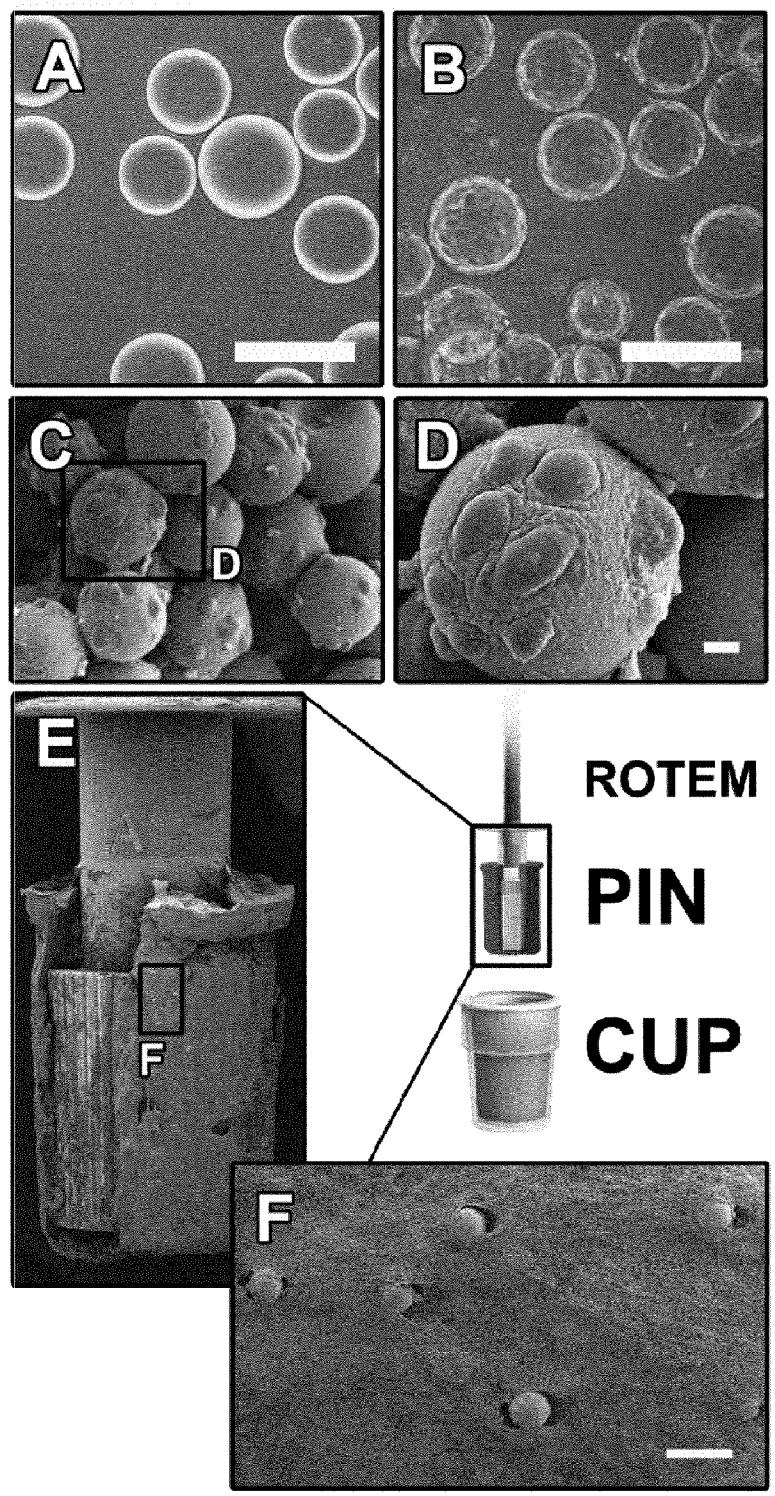

FIG. 2 shows microbead suspension in EGM-2. A uncoated B OEC-coated. Scale bar=200 μm. C SEM image of OEC-coated beads (scale bar missing) D magnification of C. Scale bar=10 μm. E Incorporation of uncoated microbeads in a ROTEM-cup-derived whole blood clot. F Magnified section of E. Scale bar=200 μm.

FIG. 3 shows (A) reduction of CT by increasing suspension volumes of either uncoated beads or beads coated with OECs, with
(+TNF) or without overnight TNFα preincubation. (B) results with increasing suspension volumes of beads coated with HUVEC with (+TNF) or without overnight TNFα incubation. Individual values are displayed as negative percentage of a simultaneously measured vehicle control. Error bars represent mean±SD. (*p<0.05, p<0.01, *p<0.001).

Figure 4:
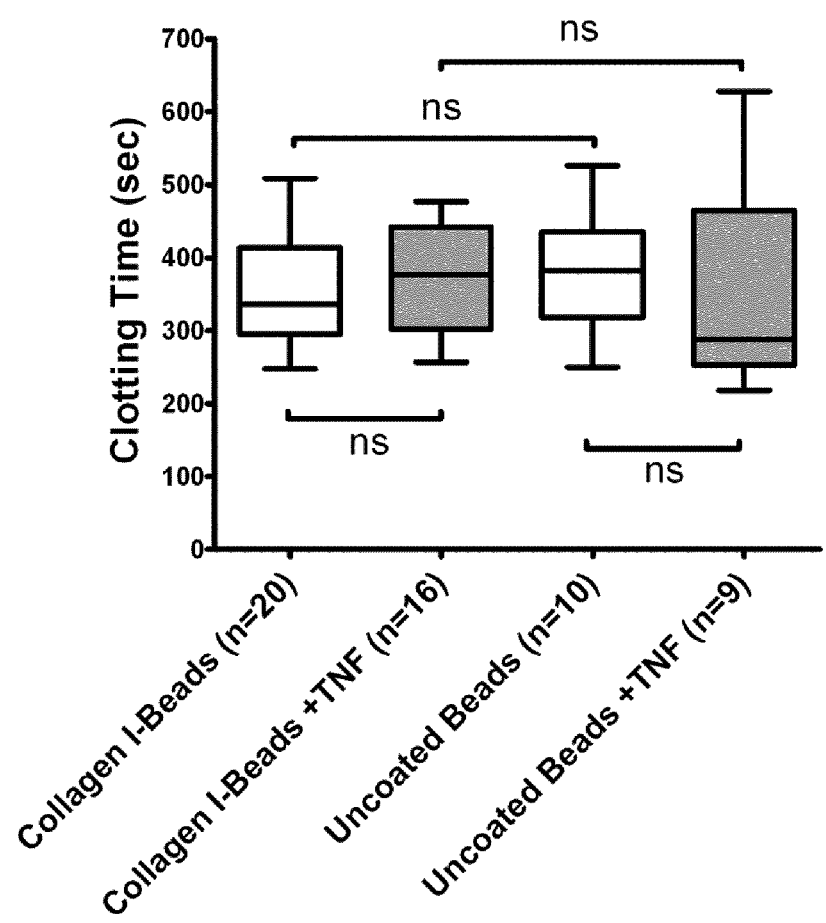

FIG. 4 shows the impact of bare beads, collagen-coating and TNFα on CT. Blood was pooled with 50 μl of Cytodex 1 (uncoated) and collagen-coated Cytodex 3 beads with optional overnight TNFα preincubation (+TNF). Error bars represent mean±SD. (ns=not significant).

FIG. 5 shows (A) impact of procoagulant mediators released into the supernatant fluid of bead suspensions upon stimulation. Supernatants (SN) were harvested from bead suspensions coated with either OEC or HUVEC that had been optionally preincubated with TNFα (+TNF). (B) Inhibition of TF in bead suspension supernatants. Blood was pooled with 50 μl of unconditioned medium (CTRL) or supernatant fluid from beads coated with either unstimulated (unstim) or TNFα preincubated (+TNF) OEC and HUVEC. Optionally the supernatants were incubated with an inhibiting antibody against human TF (+AntiTF). If not otherwise indicated by brackets, measurements are compared with CTRL. Error bars represent mean±SD. (ns=non-significant, * p<0.05, p<0.01, *p<0.001).

EXAMPLES

Materials and Methods

Cell Culture

The study was approved by the local ethics committee of the AUVA and was performed according to standards of good clinical practice. In order to enable a future autologous setting (endothelial cells and blood obtained from the same donor) it was referred to OEC in the present experiments but findings were substantiated with HUVEC, a well-characterized endothelial model. With reference to a well-established protocol, OEC were derived from Endothelial Progenitor Cells (EPC), a small subset of Mononuclear Cells (MNC) present in peripheral blood (Fuchs et al., Biomaterials 27(2006): 5399-5408). Blood samples for isolation of MNC were obtained from healthy donors after giving informed written consent. OEC were cultured in endothelial growth medium-2 (EGM-2, Lonza, Walkersville, Md., USA) and were identified by their morphology, by qPCR and flow cytometry. Endothelial phenotypes of the OEC included in the coagulation assay according to the present invention were confirmed by assessing expression patterns of endothelial markers CD31, VE-cadherin and VEGFR-2 as described elsewhere (Holnthoner et al. J. Tissue Eng. Regen. Med. (2012): DOI: 10.1002/term). To confirm the present findings with a well-established endothelial model, experiments were repeated with HUVEC-coated microbeads. HUVEC were purchased from Lonza (Walkersville, Md., USA) and were cultured in EGM-2.

To seed endothelial cells on microbeads, an approximate cell count of 400 OEC or HUVEC per bead was mixed with Cytodex 3 (collagen-coated) dextran microcarrier beads (GE Healthcare Bio-Sciences AB, Uppsala, Sweden) in 1 ml of EGM-2 medium. Beads and cells were incubated at 37° C. and 5% $CO_2$ for 4 h and shaken gently every 20 min. After transferring the suspension to a 25-$cm^2$ tissue culture flask (Greiner Bio-One, Linz, Austria), microbeads were optionally incubated with TNFα (Sigma Aldrich, Vienna) at a final concentration of 10 ng/ml for 12-16 h at 37° C. and 5% $CO_2$ in 4 ml of EGM-2 to simulate an inflammatory situation. To assess the influence of collagen, data from bare, collagen-coated Cytodex 3 were compared with uncoated Cytodex 1 (GE Healthcare Bio-Sciences AB, Uppsala, Sweden) beads in an identical setting.

Preparation of Culture Supernatant and Bead Suspensions

Coated Beads and overnight-conditioned cell culture supernatant were gently taken up with a 10 ml serological pipet and transferred to a 15 ml Falcon tube. Once beads descended, the supernatant was carefully transferred to 1.5 ml tubes and centrifuged at 1,500×g for 20 minutes. Supernatants were frozen at −80° C. immediately for further analysis while at least 200 μl left in the tubes were discarded to avoid contamination with whole cells and debris. Beads were resuspended with fresh, prewarmed EGM-2 (37° C.) by gently tipping against the wall of the tube. Again, the supernatant was discarded after sedimentation. To remove non-adherent cells and cellular debris, this step was repeated three times with prewarmed PBS. In order to achieve a 1:1 bead to medium volume ratio in bead suspensions, 5 ml of EGM-2 was added and equalized to the beads packed volume by aspiration. The bead suspensions served as a stock for subsequent dilution, were kept in a 37° C. warming block throughout all experiments and were processed within 3 hours. A schematic work flow chart of the procedure is given in FIG. 1.

ROTEM

ROTEM (TEM Innovation, Munich, Germany) uses a rotating pin that is vertically immersed into a prewarmed cup containing the blood sample and can be performed simultaneously on four channels within the same device. Coagulation of the usually citrated blood sample is initiated by recalcification and is detectable as the forming fibrin clot between the pin and the cup's wall reduces the rotation range of the pin. The generated signal is converted into a curve that gives an indication for the time point of clotting initiation, the quality of the involved factors and the onset of fibrinolysis.

After written informed consent was obtained from a healthy volunteer with no history of coagulopathy and/or anticoagulant/antiplatelet therapy, blood was taken using minimal stasis from an antecubital vein through a 21-gauge needle. After discarding the first 3 ml, blood was collected in 3.5 mL tubes (Vacuette; Greiner Bio-One, Linz, Austria) containing 0.3 mL buffered 3.2% trisodium citrate. Samples were kept in a prewarming stage at 37° C. for at least 10 minutes prior to analysis and were processed within 3 hours. ROTEM analysis of the WB sample was started by recalcification with addition of 20 μL of $CaCl_2$ (star-TEM®, 200 mmol/L) according to the manufacturers protocol.

Microbead suspensions or supernatants were added directly to the cup immediately after recalcification of citrated blood and mixed by gently pipetting up and down. The final reaction volume per ROTEM cup was 370 μl, consisting of 300 µl of citrated whole blood, 20 µl of CaCl$_2$ and 50 µl of bead suspension/supernatant. To assess concentration-dependent changes in TEM parameters 0, 5, 20 and 50 µl of the original stock solution was diluted with EGM-2 up to the final 50 µl reaction volume.

The following ROTEM parameters were calculated from the signal and included in the statistical analysis: Clotting time (CT, sec), latency until the clot reaches a firmness of 2 mm; measure for initial thrombin and fibrin formation. Clot formation time (CFT, sec), time from CT until clot reaches a firmness of 20 mm; indicates platelet function and fibrinogen quality. Alpha-angle ($\alpha$, °), angle between the x-axis and the tangent of the forming curve starting from CT point; comparable with CFT. Maximum clot firmness (MCF, mm), maximum amplitude of the curve; indicates the absolute strength of the clot. A30 (mm), clot firmness after 30 minutes.

Inhibition of Tissue Factor Activity

To assess the impact of soluble endothelial mediators an equal volume of cell culture supernatant was added, diluted with EGM-2 to the NATEM tests.

Conditioned medium was harvested from TNF-$\alpha$-stimulated and -unstimulated overnight microbead cultures and was processed as pointed out earlier. To examine the assumed impact of endothelium-derived TF culture supernatants were preincubated with an inhibitory antibody for amino acids 1-25 within the tissue factor extracellular domain (American Diagnostica mouse anti-human TF, 0.5 mg/ml, ADG4509, clone IIID8). Previous experiments have shown that this antibody could rescue whole blood CT reduction in the presence of extrinsic TF (Nielsen et al. Anaesth. Analg. 104 (2007): 59-64). The antibody was employed under gentle movement at a dilution of 1:50 for 1 hour at 37° C. on a custom-made rotation shaker.

Microscopy

Before and after ROTEM analysis, aliquots of the stock solution were examined for endothelial cell adherence and quantity by phase contrast microscopy (Zeiss).

Cups were removed from the device after A30 was generated and fixed with buffered 4% formalin at 4° C. After a washing step with PBS the blood clot along with the pin was gently extracted from the cup and dehydrated in a graded series of alcohol. Samples were chemically dried with hexamethyldisilazane, mounted on stubs, sputter-coated with palladium gold and analysed on a Scanning Electron Microscope (SEM, Jeol JSM-6510).

Statistical Analysis

Since reference values for non-activated thromboelastometry (NATEM) parameters are reported to be subject to strong variation, Clotting Time (CT), Clot Formation Time (CFT), Maximum Clot Firmness (MCF), alpha angle ($\alpha$) and A30 were converted to the percentage of the respective, simultaneously measured vehicle control. Data were included in an Excel data sheet, analyzed with GraphPad Prism 5 (GraphPad Software Inc., La Jolla, Calif., USA) software and were indicated as the mean±standard deviation. Based on a Kolomorogov-Smirnov-test data were determined to be not normally distributed. A Mann-Whitney test was therefore applied to compare values from corresponding suspension volumes (5, 20, 50 µl) in respective groups (bare vs. cell-coated, unstimulated vs. stimulated). P-Values<0.05 were considered significant.

Results

Incorporation of Endothelial Cells in ROTEM

Adherent endothelial cells could be transferred as a suspension and hence be included in a ROTEM (FIG. 2 A-D). Effectively, phase contrast microscopic assessment of stock solutions pre- and post thromboelastometry indicated an incorporation of adherent endothelial cells into the clot throughout viscoelastic tests. Scanning electron microscopic (SEM) imaging post-analysis of blood clots from TEM cups also confirmed an even distribution of beads within coagulated blood samples. Visually there was no difference in dispersion of either cell-coated or naked beads (FIG. 2 E,F).

Impact of Endothelial Cells on ROTEM

Inclusion of endothelial cell-coated beads into the ROTEM analysis significantly reduced CT in a dose-dependent manner FIG. 3 A). Using different volumes of microbead suspensions (5, 20, 50 µl) CT was not only shortened with activated cells but also with cells that had not been stimulated with TNF$\alpha$. Addition of unstimulated cell-coated bead suspension volumes significantly shortened CT compared to an equal volume of uncoated controls. Prior activation of cells by incubation with TNF$\alpha$ resulted in a significant further shortening of CT. To confirm the present findings with EC derived from another tissue, these experiments were repeated with HUVEC-coated microbeads. Increasing suspension volumes of HUVEC-coated beads resulted in a similar shortening of CT (FIG. 3 B). Again, this enhancement of coagulation initiation was detectable with both, TNF$\alpha$-stimulated and unstimulated cells.

Bare, optionally TNF$\alpha$-preincubated bead suspensions served as a control and shortened CT to a minor degree. In contrast to significant effects on clotting initiation, clot formation parameters were not impaired in the presence of endothelium. The ROTEM parameters Clot Formation Time (CFT), Maximum Clot Firmness (MCF) and $\alpha$-angle ($\alpha$) showed no effect of endothelium-derived mediators on clotting dynamics and clot strength.

Furthermore, the expected activation of coagulation by the collagen-surface of the employed Cytodex 3 beads could not be confirmed. Actually, comparison of results from uncoated Cytodex 1 and collagen-coated Cytodex 3 beads showed no effect of collagen-coating on clotting initiation in the NATEM test (FIG. 4).

Impact of Soluble Endothelial Mediators

To indirectly analyse whether CT reduction was also associated with the endothelial release of procoagulant mediators into their environment conditioned medium was harvested from EC cultures and added to the ROTEM cup at increasing volumes. EC-cultures had optionally been incubated with TNF$\alpha$ over night. Addition of 5, 20 or 50 µl of cell culture supernatants harvested from OEC and HUVEC bead suspension reduced CT similarly to the even volume of cell-coated micro-carrier beads. Again, a prior TNF$\alpha$ incubation of the cells resulted in a significant shortening of CT in comparison to supernatants derived from untreated controls (FIG. 5 A).

Tissue Factor Inhibition

Since it was assumed that CT reduction with both, EC-coated beads and EC-conditioned medium was associated with the increased availability of cell-based and soluble TF, it was tried to restore normal CTs by specifically inhibiting TF-activity.

Therefore, bead suspensions and cell culture supernatants were incubated with an inhibitory antibody against the extracellular domain of human TF.

Preincubation of bead suspensions with the anti-TF antibody at least partially rescued the observed shortening of CT (FIG. 5 B).

When incubated with inhibiting antibody prior to thromboelastometric measurements, 50 µl of supernatant from OEC and HUVEC cultures almost reached the coagubility of an equal volume of unconditioned medium, which was referred to as a control.

Discussion

A test system including all three components of coagulation-plasma, blood cells and endothelium was successfully set up according to the present invention. The findings of the present invention demonstrate 1) that EC can effectively be incorporated into a ROTEM assay via collagen-coated microbeads, 2) an acceleration of coagulation by non-activated and activated ECs as well as 3) an endothelial release of procoagulant, TF bearing components into their environment.

Using Cytodex™ beads as microcarriers for endothelial cells adherent to a collagen matrix, spheres with a somewhat vessel-wall-like surface were incorporated in a ROTEM-based, ex vivo coagulation assay with ease of operability and reproducibility. Cytodex™ beads have been proven useful as microcarriers for adherent cells and have been used in a variety of cell culture applications including in vitro angiogenesis studies.

Since the applied microcarriers were coated with collagen I a potential effect on CT even in experiments including beads without EC was considered. Collagen, as a part of the subendothelial matrix, has a highly pro-thrombogenic potential when exposed to flowing blood. Upon injury, circulating platelets firmly adhere to fibrillar collagen via the glycoprotein IIb-IIIa receptor under low shear rates. In view of this fact accelerated binding of platelets to the collagen surface of the beads that could possibly result in a reduction of CFT was suggested. However, clotting initiation measurements with collagen-coated beads did not differ significantly from those with uncoated Cytodex 1 beads. Cytodex 3 beads are provided with a thin layer of denatured collagen, which is chemically cross-linked to dextran. According to the manufacturer this collagen layer is susceptible to enzymatic digestion by trypsin and collagenases. In this respect, the provided matrix seems to offer a suitable surface for cell adhesion but it does not appear to forward glycoprotein-mediated aggregation of platelets under shear stress.

In a recent study the thrombogenic potential of blood incubated beforehand with endothelial cells on different matrix proteins was assessed by TEG but cells were not present during coagulation measurements. CT values of blood with HUVEC that had been grown on collagen I were considerably higher than those measured with cells on otherwise compounded surfaces.

In a similar way the influence of potential traces of TNFα that had not been eliminated by the rinsing steps during the processing of bead suspensions could be disregarded. In fact, conditioned medium for supernatant experiments still contained the final concentration of TNFα for stimulation of endothelial cells. TNFα is a major mediator in inflammatory signalling in numerous cell types such as macrophages and could affect clotting of whole blood resembling lipopolysaccharide incubation. However, it is unlikely that the remaining TNFα in suspensions could induce a physiological reaction in the relatively small timeframe of thromboelastometric clotting time measurement since they were added to blood right before analysis.

With the method according to the present invention resting and activated endothelial cells were included in a ROTEM assay to trace their impact on coagulation parameters. In contrast to reasonable expectations, which suggested an anti-coagulant effect of resting endothelium in clotting assays, CT was shortened even in the presence of quiescent endothelial cells. The observed CT reduction was eminently enhanced after prior incubation of cells with TNFα. Whereas initiation of blood clotting (CT) was accelerated, clotting dynamics (CFT, α) and clot strength (MCF, A30) parameters remained unimpaired. Activation of coagulation by an increased availability of TF does not affect clot strength and polymerization dynamics. In a recent thromboelastometry study, extrinsic activation with TF has been shown to shorten CT but to leave other VET parameters unaffected.

Two different endothelial cell types, OEC and HUVEC, which were both adherent to a collagen-surface, significantly affected the onset of coagulation. Since quiescent OEC were not expected to activate coagulation the present experiments were repeated with HUVEC to reproduce the results obtained in a well-characterized endothelial model. Both cell types responded to activation with TNFα and further exaggerated CT reduction. The present results not only suggest the shifting of cells to a pro-thrombotic phenotype, but also a release of pro-coagulant mediators into the surrounding medium as a response to activation. This procoagulant pattern was still present after rinsing and the replacement of the medium. Furthermore the pro-thrombotic properties of the supernatant were not impaired by centrifugation.

Therefore it was assumed that exposing cells to TNFα induced a potent activator of coagulation, which was present in a cell-based and a soluble form. TF, which occurs in cell membranes, on the surface of shedded membrane vesicles and in a soluble isoform has been shown to abbreviate clotting time in TEG. A restoration of TF-induced shortening of CT by preincubation of the blood sample with an inhibiting anti-TF antibody was already reported in the prior art. In the present examples CT values were restored by the blockade of TF in conditioned medium with the same antibody. Several endothelial cell types upregulate TF expression in response to pro-inflammatory stimuli, shear stress and exposure to flow.

In untreated HUVEC however, TF expression usually ceases to an undetectable level with other growth media than used in this study. In view of the fact that pro-coagulant properties of OEC and HUVEC were observed even in an unstimulated state, a weak, constitutive expression of TF that probably arose from the cultivation procedure was suggest. Baseline TF expression might be driven by stimulation by various growth factors like FGF2 and VEGF in the EGM-2 full medium that was used throughout all experiments.

In contrast to the majority of endothelial subtypes in vivo, TF is expressed at the surface of cultured endothelial cells as a reaction to inflammatory cytokines. In vivo, expression of TF could only be demonstrated under septic conditions with disturbed blood flow and in conjunction with specific tumor types. Indeed, viscoelastic analysis of whole blood, stimulated with lipopolysaccharides (LPS) both in vitro and in vivo revealed an activation of blood clotting, suggestive of increased TF availability, probably from monocytes.

Moreover, several studies confirmed TF on endothelium-derived micro-particles in vitro but its presence on in vivo generated ones and their actual role in the pathogenesis of cancer, thrombosis and endotoxemia is still subject to intensive investigation. In disseminated intravascular coagulation, activated endothelium also provides the pro-thrombotic microenvironment which finally results in consumptive coagulopathy and impaired microcirculation.

Early studies on endotoxemia-induced thrombosis suggested the activation of thrombin by FXI, FXII, and plasma kallikrein. Here, the pro-coagulant effect of an inflammatory state on whole blood was associated with endothelium-derived TF. Increased availability of tissue factor has been shown to shorten CT in vitro. TF is detectable on cultured endothelial cells treated with inflammatory cytokines, on micro-vesicles released from the surface of endothelium, monocytes and platelets and has been detected in a soluble form in culture supernatants. Even though it is yet impossible to determine the localization of TF within the experimental set up according to the present invention, it is demonstrably functional and activates coagulation. Although TF, as the primary activator of coagulation, is expressed in the endothelial and leukocyte response to inflammatory cytokines like IL-1 or TNF, its role in systemic inflammatory coagulation responses is still under discussion. In vitro studies reveal the expression of TF and the release of microparticles in HUVEC upon activation but it seems difficult to apply these data to endothelial function during hemostasis in health and disease.

However, direct interaction of endothelium with blood coagulation is difficult to assess as it depends on data from cell culture flow models or includes elaborate imaging techniques in vivo. Common in vitro flow systems and coagulation assays with a view to combine endothelial mediators and blood components are usually based on routine laboratory tests. Since there was interest in the ability of endothelium to directly interfere with clotting initiation, the microcarriers comprising the endothelial cells were incorporated in the novel assay according to the present invention that was capable of detecting the onset of whole blood coagulation. The approach according to the present invention with endothelium coated beads in whole blood delivered highly reproducible results concerning clotting initiation under simulated inflammatory conditions.

CONCLUSIONS

With the present invention a novel viscoelastic assay is provided introducing EC-carrying microbeads into TEM, especially ROTEM, with ease of operability and reproducibility. Driven by the ROTEM-device's rotating pin, microbeads were homogeneously distributed within the blood sample, likely exposing endothelial cells to low shear forces.

By introducing EC into VET, it was possible to trace a cellular mechanism underlying hemostasis under physiological and pathological conditions, namely a reduction of CT in whole blood. The findings according to the present invention show a direct activation of coagulation by EC on microbeads, especially when activated with TNF. Moreover, there is a strong evidence for the release of TF-bearing components into the cellular environment.

ABBREVIATIONS

EC=Endothelial Cells
A30=Clot firmness after 30 minutes
CT=Clotting Time
CFT=Clot Formation Time
DIC=Disseminated Intravascular Coagulation
EGM-2=Endothelial Growth Medium 2
HUVEC=Human Umbilical Vein Endothelial Cells
MCF=Maximum Clot Firmness
NATEM=Non Activated Thromboelastometry
OECs=Outgrowth Endothelial Cells
PBS=Phosphate Buffered Saline
qPCR=quantitative Polymerase Chain Reaction
SEM=Scanning Electron Microscopy
TEM=Thromboelastometry
TF=Tissue Factor
vWF=van Willebrand Factor
WB=Whole Blood
VEGF=Vascular Endothelial Growth Factor
VET=viscoelastic test
FGF2=Fibroblast Growth Factor 2
FI-XIII=Coagulation factors I-XIII

The invention claimed is:

1. A method for measuring coagulation of a blood or plasma sample comprising performing a viscoelastic test to measure coagulation of said sample, wherein the measuring is performed in the presence of endothelial cells immobilized on a microcarrier.

2. The method of claim 1, wherein the viscoelastic test is rotation thromboelastometry or thromboelastography.

3. The method of claim 2, wherein the endothelial cells are immobilized on microbeads.

4. The method of claim 2, wherein the endothelial cells are immobilized on microbeads comprising dextran.

5. The method of claim 4, wherein the endothelial cells are outgrowth endothelial cells, human umbilical vein endothelial cells, human dermal microvascular endothelial cells, or human saphenous vein endothelial cells.

6. The method of claim 2, wherein the endothelial cells are outgrowth endothelial cells, human umbilical vein endothelial cells, human dermal microvascular endothelial cells or human saphenous vein endothelial cells.

7. The method of claim 1, wherein the endothelial cells are immobilized on microbeads.

8. The method of claim 7, wherein the endothelial cells are outgrowth endothelial cells, human umbilical vein endothelial cells, human dermal microvascular endothelial cells, or human saphenous vein endothelial cells.

9. The method of claim 7, wherein the microbeads comprise a collagen matrix to which the endothelial cells are adhered.

10. The method of claim 1, wherein the endothelial cells are outgrowth endothelial cells, human umbilical vein endothelial cells, human dermal microvascular endothelial cells, or human saphenous vein endothelial cells.

11. The method of claim 1, wherein the endothelial cells are immobilized on microbeads comprising dextran.

12. The method of claim 1, wherein the measuring comprises rotating a pin in a cup containing the blood or plasma and the immobilized endothelial cells.

13. The method of claim 1, wherein the immobilized endothelial cells are suspended in the blood or plasma during the measuring.

14. The method of claim 1, wherein the measuring is performed in the presence of $CaCl_2$.

15. The method of claim 1, comprising, during the measuring, identifying a point in time of clotting initiation of the blood or plasma sample.

16. The method of claim 1, further comprising determining a speed of clot formation of the blood or plasma sample.

17. The method of claim 1, wherein the endothelial cells comprise human umbilical vein endothelial cells.

18. The method of claim 1, wherein the endothelial cells comprise outgrowth endothelial cells.

19. The method of claim 1, wherein the endothelial cells are activated.

20. The method of claim 19, wherein the endothelial cells are activated by incubation with TNFa.

21. The method of claim 1, wherein said microcarrier comprises glass, polystyrene, polypropylene, acrylamide, porcine gelatin or dextran.

* * * * *